(12) United States Patent
Macknik et al.

(10) Patent No.: US 11,344,226 B2
(45) Date of Patent: *May 31, 2022

(54) SYSTEMS AND METHODS FOR NON-INTRUSIVE DRUG IMPAIRMENT DETECTION

(71) Applicants: Dignity Health, San Francisco, CA (US); Arizona Board of Regents on Behalf of Arizona State University, Scottsdale, AZ (US)

(72) Inventors: Stephen L. Macknik, Anthem, AZ (US); Susana Martinez-Conde, Anthem, AZ (US); Richard E. Dale, Scottsdale, AZ (US); Richard Besserman, Phoenix, AZ (US); Troy Lee McDaniel, Chandler, AZ (US)

(73) Assignees: ARIZONA BOARD OF REGENTS ON BEHALF OF ARIZONA STATE UNIVERSITY, Scottsdale, AZ (US); DIGNITY HEALTH, San Francisco, CA (US)

(*) Notice: Subject to any disclaimer, the term of this patent is extended or adjusted under 35 U.S.C. 154(b) by 314 days.

This patent is subject to a terminal disclaimer.

(21) Appl. No.: 16/428,791

(22) Filed: May 31, 2019

(65) Prior Publication Data
US 2020/0022622 A1 Jan. 23, 2020

Related U.S. Application Data

(63) Continuation of application No. 15/306,892, filed as application No. PCT/US2015/027730 on Apr. 27, 2015, now Pat. No. 10,376,183.

(Continued)

(51) Int. Cl.
*A61B 5/11* (2006.01)
*A61B 5/18* (2006.01)
(Continued)

(52) U.S. Cl.
CPC ............ *A61B 5/1104* (2013.01); *A61B 3/113* (2013.01); *A61B 5/163* (2017.08); *A61B 5/18* (2013.01); *A61B 5/4845* (2013.01); *A61B 5/746* (2013.01)

(58) Field of Classification Search
CPC ....... A61B 5/1104; A61B 5/163; A61B 3/113; A61B 5/18; A61B 5/4845; A61B 5/746;
(Continued)

(56) References Cited

U.S. PATENT DOCUMENTS

| 4,815,839 A | 3/1989 | Waldorf |
| 5,137,345 A | 8/1992 | Waldorf |

(Continued)

FOREIGN PATENT DOCUMENTS

| CA | 2674542 | 10/2012 |
| CA | 2720962 | 6/2016 |

(Continued)

OTHER PUBLICATIONS

Applicant Initiated Interview Summary for U.S. Appl. No. 15/317,339, dated Apr. 12, 2019.

(Continued)

*Primary Examiner* — Patrick Fernandes
(74) *Attorney, Agent, or Firm* — Quarles & Brady LLP

(57) ABSTRACT

Systems and methods for detecting onset, presence, and progression of particular states, including intoxication, include observing eye movements of a subject and correlating the observed movements to known baseline neurophysiological indicators of intoxication. A detection system may record eye movement data from a user, compare the eye movement data to a data model comprising threshold eye movement data samples, and from the comparison make a determination whether or not intoxication or impairment is present. The detection system may alert the user to take (Continued)

corrective action if onset or presence of a dangerous condition is detected. The eye movements detected include saccadic and intersaccadic parameters such as intersaccadic drift velocity. Measurements may be collected in situ with a field testing device. An interactive application may be provided on a user device to provoke the desired eye movements during recording.

19 Claims, 2 Drawing Sheets

Related U.S. Application Data

(60) Provisional application No. 62/010,600, filed on Jun. 11, 2014, provisional application No. 61/986,032, filed on Apr. 29, 2014.

(51) Int. Cl.
  *A61B 5/00* (2006.01)
  *A61B 5/16* (2006.01)
  *A61B 3/113* (2006.01)

(58) Field of Classification Search
  CPC ......... A61B 5/165; A61B 5/0091; A61B 5/16; A61B 5/4064; A61B 5/6821; A61B 3/0025; G06K 9/00335; G06K 9/00604; G06K 9/00597
  See application file for complete search history.

(56) References Cited

U.S. PATENT DOCUMENTS

| | | | |
|---|---|---|---|
| 5,422,690 A * | 6/1995 | Rothberg | A61B 3/112 351/209 |
| 6,120,461 A | 9/2000 | Smyth | |
| 7,027,621 B1 | 4/2006 | Prokoski | |
| 7,857,452 B2 | 12/2010 | Martinez-Conde | |
| 7,881,493 B1 | 2/2011 | Edwards | |
| 8,348,428 B2 | 1/2013 | Martinez-Conde | |
| 8,373,106 B2 | 2/2013 | Macknik | |
| 8,668,337 B2 | 3/2014 | Waldorf | |
| 8,721,081 B2 | 5/2014 | Martinez-Conde | |
| 9,101,312 B2 | 8/2015 | Waldorf | |
| 9,301,679 B2 | 4/2016 | Martinez-Conde | |
| 9,763,573 B2 | 9/2017 | Distasi | |
| 9,962,119 B2 | 5/2018 | Macknik | |
| 10,231,617 B2 | 3/2019 | Macknik | |
| 2004/0181168 A1 | 9/2004 | Plant et al. | |
| 2006/0202841 A1 | 9/2006 | Johns | |
| 2007/0017534 A1 | 1/2007 | Thorpe | |
| 2007/0132950 A1 | 6/2007 | Victor et al. | |
| 2007/0265507 A1 | 11/2007 | De Lemos | |
| 2008/0188777 A1 | 8/2008 | Bedziouk | |
| 2009/0318773 A1 | 12/2009 | Jung | |
| 2010/0010370 A1 | 1/2010 | De Lemos et al. | |
| 2010/0100001 A1 | 4/2010 | Aguilar | |
| 2010/0277693 A1 | 11/2010 | Martinez-Conde | |
| 2010/0324454 A1 | 12/2010 | Kircher | |
| 2012/0083668 A1 * | 4/2012 | Pradeep | A61B 5/4809 600/300 |
| 2012/0215390 A1 | 8/2012 | Wang | |
| 2013/0139258 A1 | 5/2013 | Tegreene | |
| 2013/0278899 A1 | 10/2013 | Waldorf | |
| 2013/0336547 A1 | 12/2013 | Komogortsev | |
| 2014/0114148 A1 | 4/2014 | Shepherd | |
| 2016/0019410 A1 | 1/2016 | Komogortsev | |
| 2016/0022137 A1 | 1/2016 | Wetzel | |
| 2016/0250355 A1 | 9/2016 | Macknik | |
| 2017/0000339 A1 | 1/2017 | Di Statsi | |
| 2017/0258368 A9 | 2/2017 | Macknik | |
| 2017/0119296 A1 | 5/2017 | Macknik | |
| 2017/0135577 A1 | 5/2017 | Komogortsev | |

FOREIGN PATENT DOCUMENTS

| | | |
|---|---|---|
| EP | 2490584 | 2/2019 |
| WO | 2012103470 | 8/2012 |
| WO | 2015191809 | 12/2015 |

OTHER PUBLICATIONS

Benitez, Jaime T. "Eye-tracking and optokinetic tests: Diagnostic significance in peripheral and central vestibular disorders." The Laryngoscope 80.6 (1970): 834-848.
The International Search Report as dated Sep. 17, 2015 for International Application No. PCT/US2015/035253.
Extended European Search Report for Application 15786251.7, dated Dec. 15, 2017, 7 pages.
Extended European Search Report for Application 15806106.9, dated Jan. 23, 2018, 8 pages.
IP Australia Examination Report No. 1 for Application 2015253487, dated Mar. 15, 2019, 4 pages.
IP Australia Examination Report No. 1 for Application 2015274601, dated Feb. 19, 2019, 3 pages.
Office Action for U.S. Appl. No. 15/317,339, dated Jan. 2, 2019.
Written Opinion of the International Searching Authority as dated Sep. 17, 2015 for International Application No. PCT/US2015/035253.
International Search Report & Written Opinion under dated Jul. 24, 2015 in connection with PCT/US2015/027730.

* cited by examiner

SYSTEMS AND METHODS FOR NON-INTRUSIVE DRUG IMPAIRMENT DETECTION

CROSS-REFERENCE TO RELATED APPLICATION(S)

This application is a continuation of U.S. application Ser. No. 15/306,892 filed Oct. 26, 2016, now U.S. Pat. No. 10,376,183, issued Aug. 13, 2019, which is a 371 application of PCT/US2015/027730 filed Apr. 27, 2015, which claims priority to U.S. Provisional Patent Application Ser. No. 62/010,600 filed on Jun. 11, 2014, and Provisional Patent Application Ser. No. 61/986,032 filed on Apr. 29, 2014, all of which are incorporated by reference herein for all purposes.

BACKGROUND OF THE DISCLOSURE

The present disclosure generally relates to systems and methods for acquiring data from a subject and, more particularly, to systems and methods for gathering and analyzing information about the subject's eye movements to detect a temporary neurologic abnormality or to predict a state of the subject, including the presence of conditions such as alcohol, marijuana, and other illicit or prescribed drug intoxication.

Given the legalization of marijuana (*Cannabis*) for medicinal use in over twenty states, and the potential for complete legalization over time, there is a need to increase awareness and education of the general public regarding the safety risks of driving a vehicle or operating heavy equipment when impaired.

Whether the use of marijuana is legal or illegal, all marijuana users should understand that being impaired places the driver, passengers, and the general public at significant risk. Though this issue also applies to all illicit (cocaine, non-medical opiates) and legal (codeine and other medications) mind-altering substances, it is especially true with marijuana, where the user may become impaired and not realize that the drug has clouded his judgment regarding the operation of a motor vehicle. There is a general misconception that marijuana poses little risk to the driving public, and that notion must be changed through appropriate public health messaging directed at medical marijuana card-holders.

There are significant physiological differences between the use of alcohol and marijuana, and it is likely that users of marijuana may discount the potential deleterious effects of its active ingredient, tetrahydrocannabinol (THC). What may compound the problem further is the potential to use more than one substance, such as a combination of alcohol, marijuana, and/or another drug or a controlled medication, with synergistically intoxicating results.

Marijuana usage has been widespread for decades, but its legal use for medical and recreational purposes is fairly new, and its precise and objective effect on driver impairment is largely unknown. A similar gap in knowledge existed for alcohol until a widespread system of standardized field sobriety testing was implemented. By combining field sobriety testing, breathalyzer testing, and blood-alcohol testing, legislatures were enabled to establish appropriate limits on the safe use of alcohol by drivers. However, there is no comparable "Breathalyzer" or a reproducible blood level test to detect marijuana use and related impairment.

Early and objective detection of the physiological effects of marijuana and other psycho-active drug use can prevent impaired operation of motor vehicles, among other preventative measures. Considering the above, there continues to be a clear need for rapid, accurate, and non-invasive individualized systems and methods for detecting the presence or onset of drug intoxication.

BRIEF SUMMARY

The present invention overcomes drawbacks of previous technologies by providing systems and methods that afford a number of advantages and capabilities not contemplated by, recognized in, or possible in traditional system or known methodologies related to tracking or determining a subject's state, including the detection of intoxication by marijuana, opiates, codeine, alcohol, and other drugs.

In one embodiment of the present invention, systems and methods are provided for monitoring, recording, and/or analyzing eye movements in situ to determine whether oculomotor dynamics are being affected by the onset or presence of intoxication. In one aspect, a sensor arrangement may include a camera and recording assembly for detecting and recording the eye movements.

In some contemplated embodiments, systems and methods using in situ testing of eye movement dynamics may be employed to identify the onset or presence of states or physiological conditions, such as fatigue, hypoxia, stroke, intoxication, seizure, and other conditions. Eye saccades and the velocity of intersaccadic eye drift are detectably affected by the onset or presence of these conditions. A system and method may alert a user to the presence of these states or conditions in a testing environment. In particular, a system in accordance with the present invention may include devices and device assemblies that record baseline data of a subject and generate a data model representing the eye movement data of the subject, and further the system may include device and device assemblies that record eye movement data in situ and compare it to the data model to determine if the user is experiencing or about to experience any of the dangerous conditions.

In a contemplated embodiment of the present invention, a system includes a sensing arrangement that collects eye movement data of a user, and a control unit in communication with the sensing arrangement. The control unit may be configured to compare the eye movement data to one or more baseline measurements of eye movement dynamics and, if the eye movement data diverges from one or more of the baseline measurements by a threshold amount, generate an alert for delivery to the user. Comparing the eye movement data to the baseline measurements may include calculating a current intersaccadic drift velocity of the user and comparing the current intersaccadic drift velocity to one or more threshold drift velocities of the baseline measurements. The eye movement data may include one or more saccade parameters, and comparing the eye movement data to the baseline measurements may include calculating a current intersaccadic drift velocity of the user from the saccade parameters and comparing the current intersaccadic drift velocity to one or more threshold drift velocities of the baseline measurements. The baseline measurements may include one or more bio-signatures of a substance.

In another embodiment of the present invention, a method of determining a physiological state of a user includes recording from the user eye movement data of one or both of the user's eyes, comparing the eye movement data to one or more baseline measurements, and, if the eye movement data diverges from one or more of the baseline measurements by a threshold amount, delivering an alert to the user.

The eye movement data may include one or both of saccade parameters and intersaccadic drift parameters.

In another embodiment of the present invention, systems and methods of the present invention may be combined as a kit or apparatus, whose advantages and capabilities will be readily apparent from descriptions below.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

DETAILED DESCRIPTION

Systems and methods for detecting onset, presence, and progression of particular states, including intoxication, through observation of eye movements are described herein. Acute intoxication is shown by the inventors to affect oculomotor dynamics, including saccadic metrics and intersaccadic drift metrics, with increasing severity as the intoxication progresses. In particular, intersaccadic drift velocity increases as acute intoxication develops and progresses, and select oculomotor dynamics can be tracked against a baseline to alert a subject before the effects of intoxication impair the subject's ability to perform certain actions, such as operating a motor vehicle.

The systems and methods described herein are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, specific disclosure related to the detection of impairment by marijuana is provided, although it will be appreciated that the systems and methods may be applied for detection of codeine, alcohol, or other drug use and for any subject without undue experimentation.

Using the approach of the present invention, a detection system may record eye movement data from a user, compare the eye movement data to a data model comprising threshold eye movement data samples, and from the comparison make a determination whether or not the user's brain function is suffering from or is subject to impairment by drug intoxication. The detection system may alert the user or another party to take corrective action if onset or presence of a dangerous impaired condition is detected.

Figure 1:
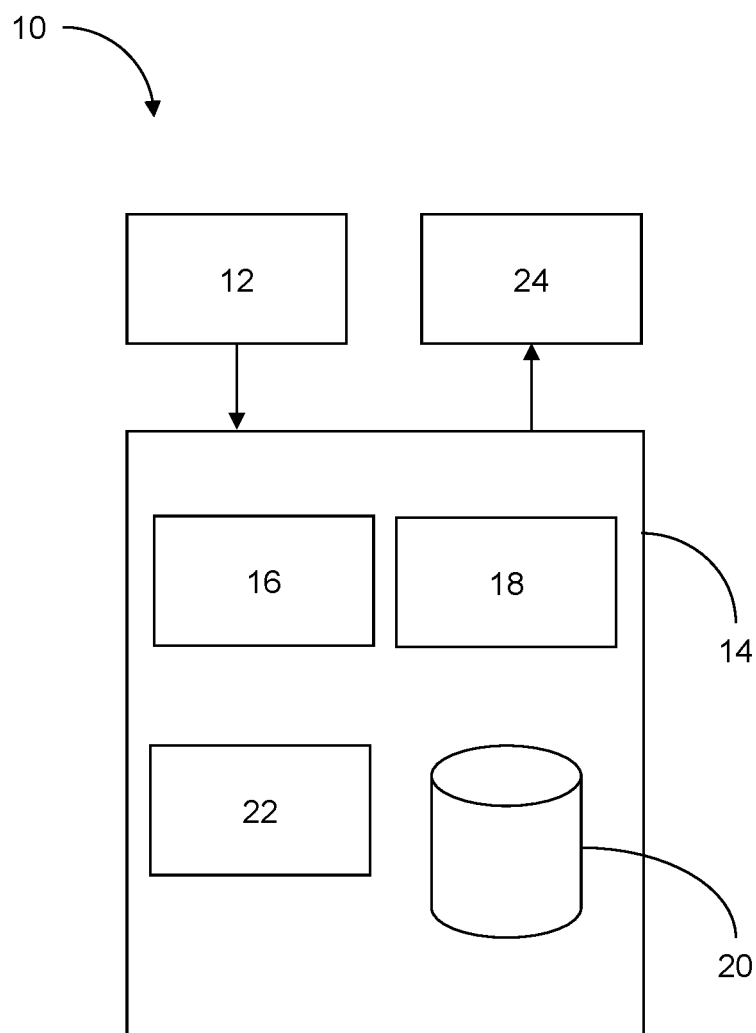
FIG. 1 is a diagram of a detection system in accordance with the present invention.

Referring to FIG. 1, an embodiment of the detection system 10 may include a sensing arrangement 12 configured to detect and record eye movement dynamics of the user. The sensing arrangement 12 may include one or more sensors suitable for collecting the eye movement data. Such sensors may include a camera or other imaging or motion tracking device capable of recording at a suitably high speed and level of detail so that the user's eye movement dynamics, including saccades and intersaccadic drift, are captured. A monocular arrangement of one or more sensors for one of the user's eyes may be used, or one or more sensors may be included for each eye to obtain binocular data. In some embodiments, the sensors may be miniaturized or otherwise compact, portable, and non-invasive. The sensors may further be vehicle-independent, and may be wireless, to facilitate integration of the sensors into any deployment of the detection system 10. For example, the sensing arrangement 12 may include sensors that are integrated into eyewear, such as on the frame or within the lenses of a pair of glasses. This allows for eye movement data collected even as the user turns his head, and allows the sensors to be positioned close to the eyes. In another example, the sensors may be integrated into a heads-up display for a vehicle. In yet another example, the sensors may be integrated into existing personal devices, such as mobile phones and tablet computers. That is, the system 10 may use the camera of the personal device in the sensing arrangement 12, and may use other native or add-on devices as well.

The sensing arrangement 12 may further include integrated or discrete devices for processing, storing, arid transmitting collected data. Such devices may include a processor, volatile and/or permanent memory, a wired or wireless transmitter, and associated power circuits and power supply for operating the devices. Software modules may define and execute instructions for operating the sensors, configuring databases, registers, or other data stores, and controlling transmission of the data. The collected data may be shared via transmission to a control unit 14 that may be integrated with or disposed physically remotely from the sensing arrangement 12. The eye movement data, or a subset thereof, may be transmitted in real-time as it is captured by the sensors, or it may be stored for later transmission.

The control unit 14 may use the processing hardware (i.e., processor, memory, and the like) of the sensing arrangement 12, or may include its own processing hardware for analyzing the eye movement data and generating an alert to the user if needed. The control unit 14 may include a plurality of modules that cooperate to process the eye movement data in a particular fashion, such as according to the methods described below. Each module may include software (or firmware) that, when executed, configures the control unit 14 to perform a desired function. A data analysis module 16 may extract information from the eye movement data for comparison to the data model. The data analysis module 16 may include one or more data filters, such as a Butterworth or other suitable bandpass filter, that retain only desired signal elements of the eye movement data. The data analysis module 16 may include program instructions for calculating, from the eye movement data, one or more eye movement dynamics, such as saccades and/or intersaccadic drift velocities, of the user's eyes. The calculation may be performed substantially in real-time, such that a calculated intersaccadic drift velocity may be considered the current drift velocity of the user's eyes.

A comparison module 18 may receive the processed eye movement data from the data analysis module 16 and may compare it to the data model as described in detail below. The control unit 14 may include or have access to a model data store 20 that stores the data model. The model data store 20 may be a database, data record, register, or other suitable arrangement for storing data. In some embodiments, the data model may simply be a threshold drift velocity, and may thus be stored as a single data record in memory accessible by the comparison module 18. In other embodiments, the data model may be a lookup table, linked list, array, or other suitable data type depending on the data samples for eye movement dynamics or bio-signatures needed to be stored in the data model.

In some embodiments, the control unit 14 may include a data model generator 22. The data model generator 22 is a module that receives eye movement data collected by the sensing arrangement 12 during a modeling step as described below. The data model generator 22 may extract, or cause the data analysis module 16 to extract, information from the collected eye movement data that will constitute the threshold eye movement data samples in the data model. The data model generator 22 may then create the data model from the threshold eye movement data samples, and may store the data model in the data model store 20. In other embodiments, the data model may be generated and stored in the data model store 20 by a separate modeling unit (not shown) of the system 10. The modeling unit may include its own sensing arrangement, processing hardware, and program modules. One suitable modeling unit may be the Eyelink 1000 by SR Research Ltd. of Mississauga, Ontario, Canada.

The control unit 14 may include or communicate with an alerting arrangement 24 configured to produce an alert to the user according to the results of the data comparison in the comparison module 18. The alerting arrangement may be any suitable indicator and associated hardware and software for driving the indicator. Suitable indicators include, without limitation: a visual display such as one or more light-emitting diodes, a liquid crystal display, a projector, and the like; a bell, buzzer, or other audible signaling means; and a piezoelectric or other vibrating device.

Figure 2:
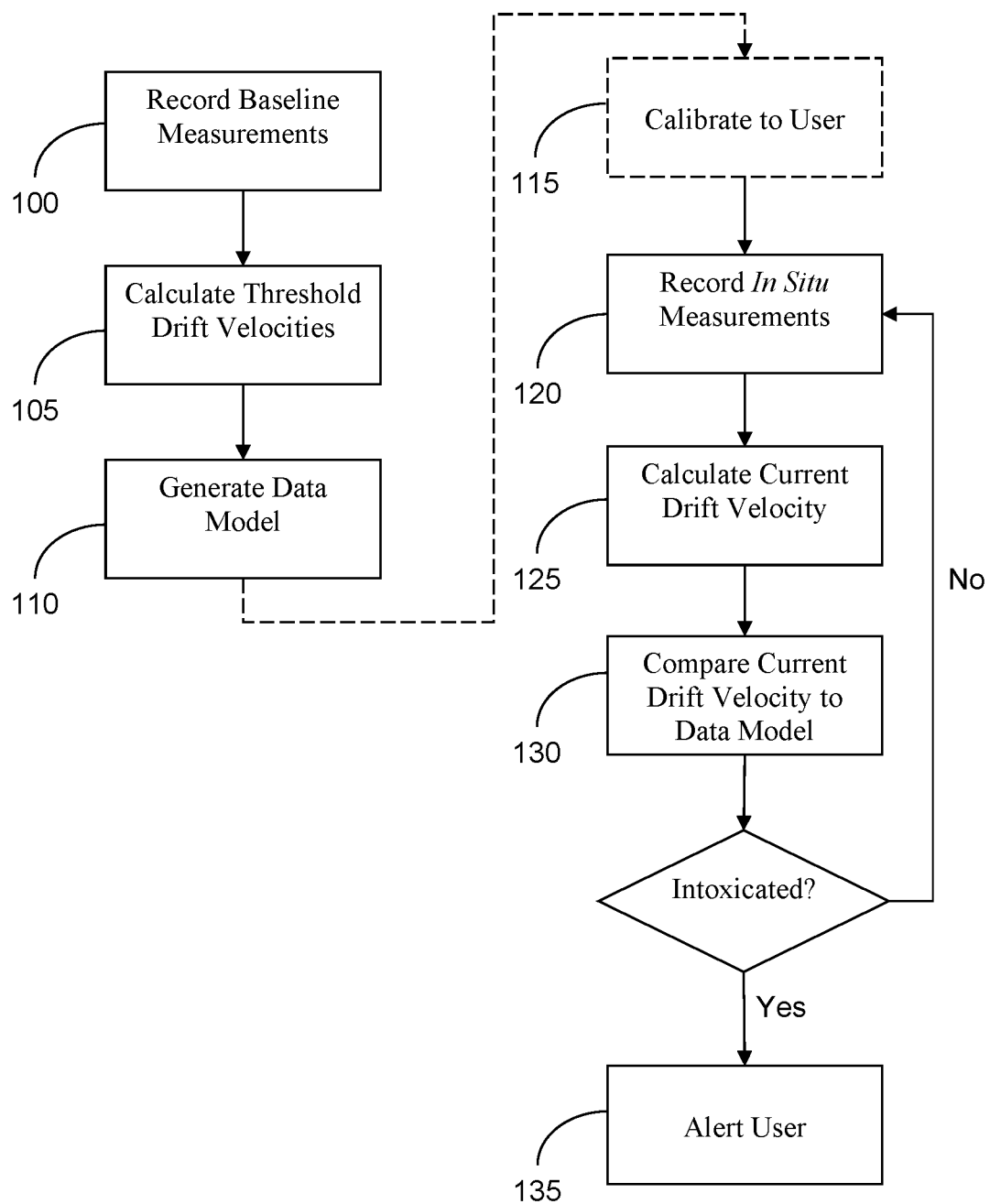
FIG. 2 is a flowchart illustrating a method for detecting intoxication in accordance with the present invention.

The detection system 10 may be used to execute any suitable method of detecting dangerous conditions that are indicated by eye movement data. Referring to FIG. 2, the detection system 10 may execute a method of detecting onset or presence of intoxication in the user. At step 100, the system may record baseline measurements of the eye movement dynamics for the data model. The baseline measurements are taken of a subject which may or may not be the user. It may be advantageous that the data model use baseline measurements of the user himself in order to individualize the operation of the system, but the baseline measurements may be taken from a non-user subject, or taken from a plurality of subjects and averaged if desired. The conditions in which the baseline measurements are recorded may depend on the desired specificity of the data model. In some embodiments, the baseline measurements may be taken in normal (i.e., sea-level or other typical atmospheric oxygen supply) conditions. In other embodiments, the baseline measurements may be taken in known intoxicated conditions. In still other embodiments, the baseline measurements may be taken continuously or at predetermined intervals as the subject is exposed to a progression from normal to intoxicated conditions. The baseline measurements may include eye movement parameters, including saccadic and microsaccadic movement, pupillary response, and eye response to light stimuli. The baseline measurements may also include eye measurements not directly related to movements, such as pupil size.

At step 105, the system may calculate one or more threshold drift velocities from the recorded baseline measurements. The threshold drift velocities may depend on the format of the collected baseline measurements. For example, where only normal-condition or only intoxicated-condition baseline measurements were taken, a single threshold drift velocity (i.e., threshold-normal or threshold-intoxicated drift velocity) may be calculated. Where progressive baseline measurements were obtained, one or more threshold drift velocities reflecting the subject's progression into, and degree of, intoxication may be calculated. Calculating the threshold drift velocities may include averaging calculated velocities from all or a portion of the individuals measured for baseline measurements. Similarly to calculation of drift velocities, any other measured parameter (e.g. pupil size or papillary response) may be calculated by averaging or normalizing the recorded baseline measurements from multiple individuals. At step 110, the system may generate the data model for the baseline-tested subject(s). The data model may represent the progression of the intersaccadic drift velocity of the subject from normal conditions to intoxicated conditions, and further beyond an intoxicated threshold into increasingly severe intoxication. The data model may be generated and stored in any suitable format that allows the system to subsequently compare eye movement data collected in situ from the user against the data model to determine the user's current impairment.

The data model may include one or more bio-signatures of neurological impairment. A bio-signature is a characteristic pattern that can be identified in measurements recorded from individuals that are exposed to particular substances. The pattern may be evident by comparing the baselines measurements of exposed individuals to those of non-exposed individuals. In some embodiments, the bio-signatures may be synthesized from the baseline measurements. The bio-signatures may be general (i.e., standardized across a population of patients, such as by demographic) or patient-specific. Bio-signatures may be unique to a particular substance, or may signify the effects of a particular group of substances. Using bio-signature identification for the data model, the system may identify which drugs and drug categories affect and/or impair brain and neurological function. The bio-signatures may correlate with drug dose and effect of the drug on key receptor sites of the central nervous system. The bio-signatures may identify any substance that can be considered impairing, such as stimulants, depressants, and hallucinogens. Non-limiting examples of drug categories that may produce an identifiable biosignature include: hallucinogens, narcotics, stimulants, depressants, cabbinoids, dissocisative anesthetics, and inhalants. Non-limiting examples of drugs that may produce an identifiable bio-signature include: ecstasy, speed, base, ice, methamphetamine, amphetamine, dexamphetamine, crystal methamphetamine, paramethoxyamphetamine, cocaine, crack cocaine, marijuana (*Cannabis*), GHB, inhalants, heroin, morphine, codiene, methadone, buprenorphine, pethidine, barbiturates, dilaudid, kapanol, MS contin, OxyCotin, lysergic acid diethylamide (LSD), psylocibin (aka magic mushrooms), phencyclidine (PCP), ketamine, and mescaline.

The steps 100, 105, 110 for obtaining the data model may be performed at any suitable time before testing the user in situ for signs of intoxication. In one embodiment, the steps 100-110 may be performed far in advance and remotely from the test environment. In another embodiment, the steps 100-110 may be performed in the test environment, immediately preceding testing the user. For example, the user may activate the system 10, such as by donning and activating eyewear housing the sensing assembly 12, which initiates step 100 of recording the baseline measurements in the present conditions. This may be in normal conditions, such as when the user is about to drive his vehicle in the morning, and only the normal eye movement data would be collected as baseline measurements. In still other embodiments, the data model may be created by the system 10 or another system using a different method than described above.

At step 115, optionally the system may calibrate itself to the user if the data model or comparison method require it. For example, the data model may be a standardized model generated from baseline measurements of (a) non-user subject(s), or the comparison method may determine the presence of intoxication from a percentage deviation from the user's threshold-normal drift velocity value(s). See below. In such an embodiment, the system calibrates (step 115) by recording a calibration set, such as ten seconds or less but preferably five seconds or less, of eye movement data of the user when the system is activated in the test environment under normal conditions. The system may compare the calibration data to the data model. In one embodiment, this involves determining a deviation of the user's threshold-normal drift velocity from the threshold-normal drift velocity of the model. The system can then adapt the data model to the user.

At step 120, the system may record in situ eye movement data from the user continuously or at predetermined intervals while the system is activated. At step 125, the system may calculate, in real-time or at predetermined intervals, the user's current drift velocity. At step 130, the system may compare the current drift velocity and other recorded user parameters to the data model to determine the user's progression (or lack thereof) toward intoxication. Such progression may be calculated within any suitable paradigm. Examples include, without limitation: ratio or percentage by which the current drift velocity exceeds the user's or the data model's threshold-normal drift velocity; ratio or percentage by which the current drift velocity is below or above the threshold-intoxicated drift velocity; comparison of current drift velocity to points on a curve between threshold-normal and threshold-intoxicated values in the data model; and the like. Additionally or alternatively, the parameters of the data model that are compared to the recorded user parameters may be taken from one or more bio-signatures within the data model, as described above. The user-to-data model comparison (step 130) may include determining whether the recorded user parameters are a match to one of the bio-signatures. If the user is neither intoxicated nor within a predetermined proximity to the threshold-intoxicated value of the data model, the system returns to step 120 and continues recording current data. If the user's condition warrants (i.e., the current drift velocity is above or within a certain range of the threshold-intoxicated value), at step 135 the system may alert the user to take corrective action. If there is a match between the recorded user parameters and one or more bio-signatures in the data model, the alert (step 135) may include an identification of the substance(s) to which the user has been exposed and which may be impairing the user.

Embodiments of the system and methods may be used by law enforcement for field sobriety testing as well as for drug education and drug recognition evaluation programs. With respect to field sobriety testing, the system may be implemented as a handheld or otherwise transportable device configured to record the eye movement dynamics of a vehicle driver or heavy equipment operator. The device may perform the analysis and matching steps locally using it native processing power and memory, or the device may transmit the recorded user parameters to a remote processing unit to perform those steps. In an example of a drug evaluation program, such as a drug recognition evaluation (DRE) program, the eye movement dynamics and analysis results may be used to supplement a series of predefined DRE tasks that are routinely performed by trained law enforcement experts, such as in addition to drawing blood to determine the present of elevated levels of alcohol or other substances. During the DRE process the eye movement dynamics may be analyzed for the presence of horizontal gaze nystagmus, pupillary size, pupillary reflex, and response to stimuli, among other parameters. For law enforcement use, security of the recorded and transmitted information may be performed under a data security framework that meets or exceeds the tenets of "chain of custody," and CJIS and/or HIPAA compliance, as required by the legal system.

Currently, there are very few principled educational systems to prepare marijuana users—even for those who are responsible medical users—to evaluate and understand the effects of individual impairment from the drug. A pilot project in accordance with this disclosure is underway to respond rapidly to meet the need. In Phase One, the collaborating parties will develop and pilot impaired driver simulation software that correlates driver impairment as a function of marijuana dosage. Due to the pressing concerns about marijuana legalization and its widespread use, the collaborators will rapidly develop and release an interactive educational tool to be made available to medical and recreational marijuana users, family members, and teachers, to explain and demonstrate the dose-related effects of marijuana on driving. This tool may be in the form of an application that operates on a smart phone (iPhone/Android/MS), an iPad or other tablet, or a computer (OS/MS Windows/Linux). The application will enable the user to estimate impairment, driving ability, and the level of impairment as a function of reported equivalent marijuana usage/dosage in terms of comparable equivalent blood-THC level. This goal of this application is to assist in reinforcing education among the users and general public of the very real dangers of driving when impaired by marijuana.

In Phase Two, the collaborators will develop an affordable eye movement recording device that is based on existing laboratory technology, to assess eye movement dynamics. The eye movements may be captured by a sensing arrangement while the subject user engages in an interactive version of the impairment application similar to the one described in Phase One of this proposal. The device will also capture pupil size and measure response to a bright light stimulus to detect neurophysiologic findings characteristic of marijuana use. The eye movement capture and analysis technology has been used in medicine to diagnose certain neurologic conditions. This technology provides a reliable and objective indicator of physiological brain impairment and will show the user of marijuana that the drug impacts brain function and causes impairment. The data obtained from the device would be used to provide educational programs.

The described system and methods may be implemented in any environment and during any task that may subject the user to dangerous conditions that affect eye movements. The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A system for detecting intoxication of a subject, the system comprising:
a sensing arrangement that collects eye movement data of the subject; and
a control unit in communication with the sensing arrangement, the control unit being configured to:
calculate corresponding values of one or more recorded eye movement dynamics from the eye movement data, the one or more recorded eye movement dynamics each representing a neurophysiological indicator of intoxication and including at least one intersaccadic parameter;
compare the corresponding values of the one or more recorded eye movement dynamics to one or more baseline measurements of eye movement dynamics to identify an intoxicated state of the subject; and
responsive to a result of the comparison indicating the presence of the intoxicated state, generate an alert for delivery to a user of the system.

2. The system of claim 1, wherein the at least one intersaccadic parameter includes one or more intersaccadic drift velocities of the subject, and comparing the corresponding values of the one or more recorded eye movement dynamics to the baseline measurements comparing the corresponding values associated with the one or more intersaccadic drift velocities to one or more threshold drift velocities of the baseline measurements.

3. The system of claim 2, wherein the control unit is further configured to identify, in the eye movement data, comprises one or more saccade parameters of each of a plurality of saccades of the subject, and to calculate the corresponding values associated with the one or more intersaccadic drift velocities from the one or more saccade parameters.

4. The system of claim 1, wherein the baseline measurements comprise one or more bio-signatures each associated with one or more of a plurality of substances, and the control unit is configured to compare the corresponding values of the one or more recorded eye movement dynamics to the one or more baseline measurements to determine whether the corresponding values indicate that one or more of the one or more bio-signatures is present in the eye movement data.

5. The system of claim 4, wherein each of the plurality of substances is a drug.

6. The system of claim 5, wherein a first substance of the plurality of substances is marijuana, a first bio-signature of the one or more bio-signatures associated with the first substance is an indicator of impairment of the subject by marijuana, and the control unit is further configured to, responsive to a determination that the first bio-signature is present in the eye movement data, generate the alert to include an indication that marijuana impairment is the intoxicated state of the subject.

7. The system of claim 4, wherein the control unit is further configured to, responsive to a determination that a first bio-signature of the one or more bio-signatures is present in the eye movement data, determine that a first substance, of the plurality of substances, is associated with the first bio-signature and include an indication of the first substance in the alert.

8. The system of claim 4, wherein the one or more bio-signatures each identify one of a plurality of categories of drugs, and the control unit is further configured to, responsive to a determination that a first bio-signature of the one or more bio-signatures is present in the eye movement data, determine that a first category, of the plurality of categories of drugs, is associated with the first bio-signature and include an indication of the first category in the alert.

9. A system for detecting intoxication of a subject, the system comprising:
a sensing arrangement that collects eye movement data of the subject;
a control unit in communication with the sensing arrangement, the control unit being configured to:
calculate corresponding values of one or more recorded eye movement dynamics from the eye movement data, the one or more recorded eye movement dynamics each representing a neurophysiological indicator of intoxication;
compare the corresponding values of the one or more recorded eye movement dynamics to one or more baseline measurements of eye movement dynamics to identify an intoxicated state of the subject; and
responsive to a result of the comparison indicating the presence of the intoxicated state, generate an alert for delivery to a user of the system;
control the sensing arrangement to record a calibration set of eye movement data of the subject under normal conditions;
calculate the one or more baseline measurements of eye movement dynamics from the calibration set of eye movement data, wherein the intoxicated state is indicated as present in the subject when the corresponding values of the one or more recorded eye movement dynamics deviate from corresponding measurements of the one or more baseline measurements by at least a corresponding threshold amount;
wherein the control unit comprises memory storing a data model and, to calculate the one or more baseline measurements, is further configured to:
obtain a first set of threshold-normal values of the eye movement dynamics from the data model;
calculate a second set of threshold-normal values of the eye movement dynamics from the calibration set of eye movement data;
determine a deviation of the second set of threshold-normal values from the first set of threshold-normal values; and
set the one or more baseline measurements based on the deviation.

10. A system for detecting intoxication of a user, the system comprising a control unit implemented in processing hardware including a processor and memory storing one or more baseline measurements of eye movement dynamics and further storing program instructions that, when executed when executed by the processor, cause the control unit to:
receive eye movement data digitally recorded in situ by monitoring the user's eye movement for a period of time;
calculate corresponding values of one or more recorded eye movement dynamics from the eye movement data, the one or more recorded eye movement dynamics each representing a neurophysiological indicator of intoxication and including at least one intersaccadic parameter;

compare the corresponding values of the one or more recorded eye movement dynamics to the one or more baseline measurements to identify an intoxicated state of the user; and responsive to a result of the comparison indicating the presence of the intoxicated state, cause a perceptible alert to be produced by an alerting arrangement.

11. The system of claim 10, wherein the at least one intersaccadic parameter includes one or more intersaccadic drift velocities of the user, and the control unit is configured to:

calculate the one or more intersaccadic drift velocities;

determine one or more threshold drift velocities from the baseline measurements; and compare the one or more intersaccadic drift velocities to the one or more threshold drift velocities to determine the presence of the intoxicated state.

12. The system of claim 11, wherein the memory further stores a data model that includes the one or more baseline measurements and represents a progression of intersaccadic drift velocity values from a normal condition to and intoxicated condition and further to a severe intoxication condition.

13. The system of claim 11, wherein one of the one or more intersaccadic drift velocities is a drift mean velocity, and wherein when the drift mean velocity is slower than the one or more threshold drift velocities by more than a threshold amount, the control unit causes the alert to be produced.

14. The system of claim 11, wherein one of the one or more intersaccadic drift velocities is a current intersaccadic drift velocity, and wherein when the current intersaccadic drift velocity is slower than the one or more threshold drift velocities by more than a threshold amount, the control unit causes the alert to be produced.

15. The system of claim 10, wherein the control unit is in electronic communication with a sensing arrangement disposed physically remotely from the control unit, the control unit controlling the sensing arrangement to collect the eye movement data in situ with the user and receiving the eye movement data from the sensing arrangement.

16. The system of claim 10, wherein the processor, the memory, and the alerting arrangement are integrated into a mobile computing device, and wherein the control unit is in electronic communication with a sensing arrangement integrated into the mobile computing device, the control unit controlling the sensing arrangement to collect the eye movement data in situ with the user and receiving the eye movement data from the sensing arrangement.

17. The system of claim 16, wherein the mobile computing device is a personal device of the user, the sensing arrangement includes a camera of the personal device, and the alerting arrangement includes one or both of a visual display of the personal device and an audible signaling means of the personal device.

18. The system of claim 17, further comprising an application presented on the personal device for interaction by the user while the eye movement data is collected.

19. The system of claim 10, wherein the intoxicated state identifiable from the baseline eye movement dynamics is a marijuana-induced intoxicated state.

* * * * *